United States Patent [19]

Gilkerson et al.

[11] Patent Number: 4,833,137

[45] Date of Patent: May 23, 1989

[54] BENZOTHIAZINONE DERIVATIVES

[75] Inventors: Terence Gilkerson; David C. Jennens; Mandy E. Coombs, all of Kent, England

[73] Assignee: Shell Internationale Research Maatschappij B.V., The Hague, Netherlands

[21] Appl. No.: 49,245

[22] Filed: May 13, 1987

[30] Foreign Application Priority Data

May 13, 1986 [GB] United Kingdom ............... 8611618

[51] Int. Cl.⁴ .................. C07D 417/02; A61K 31/54
[52] U.S. Cl. ................................. 514/224.2; 544/50
[58] Field of Search ........................ 544/50; 514/223

[56] References Cited

U.S. PATENT DOCUMENTS

| | | | |
|---|---|---|---|
| 2,978,448 | 4/1961 | Hasspacher | 544/50 |
| 3,829,488 | 8/1974 | Wolf et al. | 564/162 |
| 3,853,876 | 12/1974 | Wolf et al. | 544/372 |
| 3,881,019 | 4/1975 | Wolf et al. | 514/618 |
| 3,928,590 | 12/1975 | Wolf et al. | 514/184 |
| 4,075,336 | 2/1978 | Kondo | 514/226 |
| 4,436,739 | 3/1984 | Krumkalns | 514/226 |

FOREIGN PATENT DOCUMENTS 1545807 11/1969 Fed. Rep. of Germany .
1302657 11/1970 Fed. Rep. of Germany .
1065920 4/1967 United Kingdom .

OTHER PUBLICATIONS

Ann. Chim. (Rome), 77, vol. 67 (9–12), pp. 707–719 (1977).
Acta Chim. Acad. Sci. Hung., 75, vol. 85 (1), pp. 89–95 (1975).
Pharmazie, 69, vol. 24 (2), pp. 100–108 (1969).
Pharmazie, 67, vol. 22 (11), pp. 611–620 (1967).
Z. Chem., 67, vol. 7(6), pp. 231–232 (1967).
Justus Liebigs. Ann. Chem., 77, (8), pp. 1249–1266 (1977).
Atti Accad. Sci, Lett. Arti Palermo, Parte 1, 74, vol. 33 (2), pp. 411–420 (abstract only).

Primary Examiner—Jane T. Fan

[57] ABSTRACT

The invention provides benzothiazinone derivatives of formula

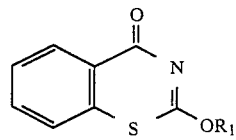

I wherein $R_1$ represents a nitrogen-containing heteroaromatic group or a phenyl group substituted by 1 or 2 substituents selected from halogen atoms, alkyl, haloalkyl and alkoxy groups; a process for the preparation of such compounds; compositions containing them and a method of combating plant pathogenic fungi using such compositions or compounds.

8 Claims, No Drawings

BENZOTHIAZINONE DERIVATIVES

This invention relates to fungicidal compositions containing benzothiazinone derivatives, certain novel benzothiazinone compounds, a process for the preparation of such compounds and a method of combating plant pathogenic fungi using such compositions or compounds.

UK Patent Specification No. 1,065,920 describes 2-substituted benzoxazinones of the formula:

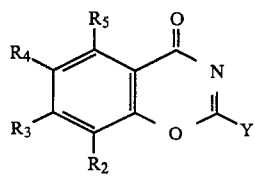

wherein each of $R_2$—$R_5$ denotes, inter alia, hydrogen, halogen, alkyl; and Y represents $OR_6$, $SR_8$ or $NR_7R_8$, $R_6$-$R_8$ being various hydrocarbon groupings, and discloses the activity of such compounds against certain fungi. The derivatives of this structure in which $R_2$, $R_3$, $R_4$ and $R_5$ all represent hydrogen atoms, Y represents a phenoxy group, a naphthyloxy group or a group -$OCH_2CCl_3$ and the heterocyclic oxygen atom is replaced by a sulphur atom are described in German Auslegeschrift 1302657 but there is no disclosure in that document of any fungicidal activity in the compounds concerned.

It has now been discovered that certain novel 2-substituted benzothiazinones possess useful fungicidal activity. According to the present invention there is therefore provided a benzothiazinone compound of the general formula I:

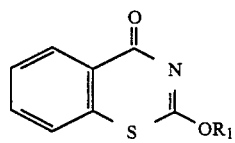

wherein $R_1$ represents a nitrogen-containing heteroaromatic group or a phenyl group substituted by 1 or 2 substituents selected from halogen atoms, alkyl, haloalkyl and alkoxy groups.

When any of the foregoing substituents represents or contains an alkyl substituent group, this may be linear or branched and may contain up to 12, preferably up to 6, and especially up to 4, carbon atoms, suitable examples being methyl, ethyl, propyl and butyl.

When $R_1$ represents a substituted phenyl group, the phenyl group may be substituted in the 2-position by an alkyl or haloalkyl group and/or in the 4-position by a halogen atom or an alkoxy group.

Preferably, $R_1$ represents a 2-trifluoromethylphenyl group, a 4-methoxyphenyl group, a 4-chloro-2-methylphenyl group or a pyridyl group.

The invention also provides a process for the preparation of compounds of the general formula I defined above, which comprises reacting a compound of formula $R_1OCN$, wherein $R_1$ is as defined above, with a compound of formula II

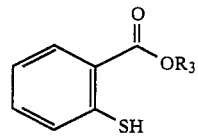

wherein $R_3$ represents a hydrogen atom or an alkyl group.

The starting compound of formula $R_1OCN$ may be conveniently prepared by reacting a compound of formula $R_1OH$ in which $R_1$ is as defined above with cyanogen bromide, suitably in an organic solvent such as acetone and, preferably, in the presence of an organic base such as triethylamine.

In the alternative, the compounds of general formula I defined above may be prepared by reacting a compound of formula $R_1OH$ with a 2-halo benzothiazinone of formula III:

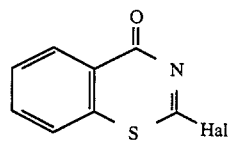

wherein Hal represents a halogen, preferably chlorine, atom and $R_1$ has the meaning defined above in relation to formula I. The reaction is conveniently carried out in an inert organic solvent, such as dichloromethane, and proceeds smoothly at room temperature. Preferably, it is carried out in the presence of a base, suitably an organic base such as a trialkylamine, triethylamine being most preferred.

The starting 2-halo-benzothiazinone of formula II may conveniently be prepared from anthranilic acid by reaction with acid/nitrite, followed by thiocyanate to form 2-thiocyanatobenzoic acid, which is then reacted with phosphorus pentachloride, suitably in an organic solvent such as an ether.

In another aspect, the invention provides a fungicidal composition which comprises a carrier together with, as active ingredient, a benzothiazinone compound of formula I as defined above. The invention includes also a method of making such a composition which comprises bringing a compound of formula I into association with at least one carrier.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products, alkali or alkaline earth metal salts, preferably sodium salts, of sulphuric or sulphonic acid esters containing at least 10 carbon atoms in the molecule, for example sodium lauryl sodium, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

Of particular interest in enhancing the duration of the protectant activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a benzothiazinone of the general formula I as defined above, and a method for combating fungus at a locus, which comprises treating the locus, which may for example be plants subject to or subjected to fungal attack, seeds of such plants or the medium in which such plants are growing or are to be grown, with such a derivative.

The present invention is of wide applicability in the protection of crop plants against fungal attack. Typical crops which may be protected include vines, grain crops such as wheat and barley, rice, beans and apples. The duration of protection is normally dependent on the individual compound selected, and also a variety of external factors, such as climate, whose impact is normally mitigated by the use of a suitable formulation.

The invention is illustrated in the following Examples.

Example 1

(A) Preparation of 2-methyl-4-chlorophenyl cyanate 4-chloro-2-methyl phenol (10g, 0.07 mol) and cyanogen bromide (7.4g, 0.07 mol) were stirred in acetone at 0° C. and triethylamine (9.7 ml, 0.07 mol) was added dropwise. The mixture was stirred at 0° C. for a further 2 hours, then filtered. The filtrate was concentrated using a rotary evaporator to leave the desired product as a fawn solid. This was used without further purification. The melting point of the product, after recrystallisation from ethyl acetate/hexane, was found to be 60° C.

| Analysis | | |
|---|---|---|
| Calc. C 57.3; | H 3.6; | N 8.4% |
| Found C 57.6; | H 3.3; | N 7.6% |

(B) Preparation of 2-(4-chloro-2-methyl)phenoxybenzothiazinone 2-methyl-4-chlorophenyl cyanate (1.8g, 0.01 mol) and ethyl 2-mercaptobenzoate (2g, 0.01 mol) were refluxed in ether (30ml) for 72 hours. The desired product was obtained by filtration as a white solid, m.pt. 144° C. (recrystallised from ethanol)

| Analysis | | |
|---|---|---|
| Calc. C 59.3; | H 3.3; | N 4.6% |
| Found C 59.8; | H 3.2; | N 4.4% |

Examples 2-4

Following procedures similar to those described in Example 1 above, further 2-substituted benzothiazinones were prepared, whose physical characteristics and analyses are given in Table I below. In this table, the compounds are identified by reference to the substituents in the following formula:

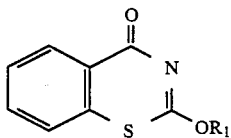

I

TABLE I

| | | | | Analysis | | | | | |
|---|---|---|---|---|---|---|---|---|---|
| | | | | C | | H | | N | |
| Example No. | X | $R_1$ | M. Pt. °C. | Calc. | Found | Calc. | Found | Calc. | Found |
| 2 | O | 2-$CF_3$ Phenyl | 144 | 55.7 | 55.6 | 2.5 | 2.1 | 4.3 | 3.7 |
| 3 | O | 4-$CH_3O$ Phenyl | 143 | 63.2 | 62.8 | 3.9 | 3.6 | 4.9 | 4.6 |
| 4 | O | 2-Pyridyl | 220 | 60.9 | 60.9 | 3.1 | 3.0 | 10.9 | 10.7 |

Example 5

The fungicidal activity of representative compounds of the invention was evaluated by means of the following tests:-

(a) Direct protectant activity against vine downy mildew (Plasmopara viticola; P.v.p)

The test is a direct protectant one using a foliar spray. The lower surfaces of leaves of whole vine plants (cv Cabernet Sauvignon) are sprayed with a solution of the test compound in 1:1 water/acetone containing 0.04% "TWEEN 20" (Trade Mark; a polyoxyethylene sorbitan ester surfactant). The spraying is carried out using a moving track sprayer giving an application rate of 1kg/ha, and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(b) Direct protectant activity against vine grey mould (Botrytis cinerea; Bcp)

The test is a direct protectant one using a foliar spray. The lower surfaces of detached vine leaves (cv Cabernet Sauvignon) are sprayed with the test compound at a dosage of 1kg/ha using a track sprayer as in (a). 24 Hours after spraying the leaves are inoculated with droplets of aqueous suspension containing $10^5$ conidia/ml. After a further 5 days in high humidity the percentage of leaf area covered by disease is assessed.

(c) Activity against wheat eyespot in-vitro (Pseudocercosporella herpotrichoides; PhI)

This test measures the in vitro activity of compounds against the fungus causing wheat eyespot.

The Test Compound is dissolved or suspended in acetone and is added to molten half strength Potato Dextrose Agar to give a final concentration of 100ppm compound and 3.5% acetone. After agar has set, plates are inoculated with 6mm diameter plugs of agar/mycelium taken from a 14 day old culture of P. herpotrichoides.

Plates are incubated at 20° C. for 12 days and radial growth from the inoculation plug is measured.

(d) Activity against Fusarium in-vitro (Fusarium species; FsI)

This test measures the in vitro activity of compounds against a species of Fusarium that causes stem and root rots.

Compound is dissolved or suspended in acetone and added to molten half strength Potato Dextrose Agar to give a final concentration of 100ppm compound and 3.5% acetone. After agar has set, plates are inoculated with 6mm diameter plugs of agar and mycelium taken from a 7 day old culture of Fusarium sp..

Plates are incubated at 20° C. for 5 days and radial growth from the plug is measured.

(e) Activity against wheat brown rust (Puccinia recondita; Pr)

The test is a direct protectant one using a foliar spray. Wheat seedlings (cv Brigand) are grown to the 1-1½ leaf stage. The plants are then sprayed with the test compound at a dosage of 1 kg/ha using a track sprayer as described under (a). Test compounds are applied as solutions or suspensions in a mixture of acetone and water (50:50 v/v) containing 0.04% surfactant ("TWEEN 20"—Trade Mark).

18-24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°-22° C. Thereafter, the plants are kept in ambient glasshouse conditions, that is, in moderate relative humidity and at a temperature of 20° C.

The disease is assessed 10 days after inoculation on the basis of the percentage of the plant covered by sporulating pustules compared with that on the control plants.

The extent of disease control in all the above tests is expressed as a rating compared with either an untreated control or a diluent-sprayed control, according to the criteria:

0 = less than 50% disease control
1 = about 50–80% disease control
2 = greater than 80% disease control The results of these tests are set out in Table II below:

TABLE II

| Ex No | Fungicidal Activity |
| --- | --- |
| 1 | Pr 1 |
| 2 | Pvp 2; Pr 1; Ph 1; Fs 1 |
| 3 | Pvp 2; Ph 1; Fs 1 |
| 4 | Bcp 1 |

We claim:

1. A benzothiazinone compound of the formula I:

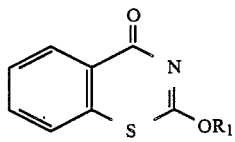

wherein $R_1$ represents a pyridyl group.

2. A fungicidal composition which comprises a carrier together with, an active ingredient, a fungicidally effective amount of a benzothiazinone compound of formula

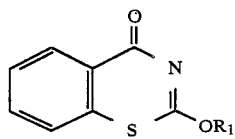

wherein $R_1$ represents a pyridyl group or a phenyl group substituted by 1 or 2 substituents selected from halogen atoms, $C_{1-12}$ alkyl, $C_{1-12}$ haloalkyl and $C_{1-12}$ alkoxy groups.

3. A composition as claimed in claim 2 wherein $R_1$ represents a phenyl group substituted in the 2-position by a $C_{1-12}$ alkyl or $C_{1-12}$ haloalkyl group and/or in the 4-position by a halogen atom or a $C_{1-12}$ alkoxy group.

4. A composition as claimed in claim 3 wherein $R_1$ represents a 2-trifluoromethylphenyl group, a 4-methoxyphenyl group or a 4-chloro-2-methylphenyl group.

5. A composition as claimed in claim 2, wherein $R_1$ represents a pyridyl group.

6. A composition as claimed in claim 2 which comprises at least two carriers, at least one of which is a surface-active agent.

7. A method of combating fungus at a locus which comprises treating the locus with a fungicidally effective amount of a compound as claimed in claim 1 or a composition as claimed in claim 2.

8. A method as claimed in claim 7, wherein the locus comprises plants subject to or subjected to fungal attack, seeds of such plants, or the medium in which the plants are growing or are to be grown.

* * * * *

UNITED STATES PATENT AND TRADEMARK OFFICE
CERTIFICATE OF CORRECTION

PATENT NO. : 4,833,137

DATED : May 23, 1989

INVENTOR(S) : TERENCE GILKERSON ET AL

It is certified that error appears in the above-identified patent and that said Letters Patent is hereby corrected as shown below:

Claim 2 (column 7, line 36), change " an " to -- as --

Signed and Sealed this

Thirteenth Day of February, 1990

Attest:

JEFFREY M. SAMUELS

*Attesting Officer*        *Acting Commissioner of Patents and Trademarks*